US00PP37102P2

(12) United States Plant Patent
Hindmarsh

(10) Patent No.: US PP37,102 P2
(45) Date of Patent: Nov. 18, 2025

(54) ***DELPHINIUM* PLANT NAMED 'Violets Are Blue'**

(50) Latin Name: *Delphinium elatum*
Varietal Denomination: Violets Are Blue

(71) Applicant: Katrina Hindmarsh, Palmerston North (NZ)

(72) Inventor: Katrina Hindmarsh, Palmerston North (NZ)

( * ) Notice: Subject to any disclaimer, the term of this patent is extended or adjusted under 35 U.S.C. 154(b) by 0 days.

(21) Appl. No.: 18/831,574

(22) Filed: Apr. 30, 2025

(51) Int. Cl.
*A01H 6/72* (2018.01)
*A01H 5/02* (2018.01)

(52) U.S. Cl.
USPC ..... Plt./423

(58) Field of Classification Search
USPC ..... Plt./423
CPC ..... A01H 6/72; A01H 5/02
See application file for complete search history.

*Primary Examiner* — Keith O. Robinson

(57) ABSTRACT

A new and distinct *Delphinium* plant named 'Violets are Blue' of large semi-double flowers with purple petals that have a ruffled bluish edge and a purple and white center bee on heavily-branched, strong, upright stems that withstand wind and rain without staking. The new plant has a compact and sturdy plant habit and excellent garden performance, and is useful for landscaping, as a specimen or en masse, and as a cut flower.

2 Drawing Sheets

Botanical designation: *Delphinium elatum.*
Cultivar denomination: 'Violets Are Blue'.

STATEMENT REGARDING PRIOR DISCLOSURES UNDER 37 CFR 1.77(B)(6)

The Applicant asserts that no publications, advertisements relating to sales, offers for sale, or public distribution occurred more than one year prior to the effective filing date of this application. Any information about the claimed plant would have been obtained from a direct or indirect disclosure from the applicant. Applicant claims a prior art exception under 35 U.S.C. § 102(b)(1) for any disclosure or sales prior to the filing date but less than one year prior to the effective filing date.

BACKGROUND OF THE INVENTION

The present invention relates to a new and distinct cultivar of *Delphinium* plant, botanically known as *Delphinium elatum*, useful as a perennial garden plant and cut flower and hereinafter referred to by the name 'Violets Are Blue'.

The new *Delphinium* plant is a product of a planned breeding program conducted by the hybridizer, Katrina Hindmarsh, in a commercial garden in Whanganui, New Zealand. The objective of the breeding program is to create new strong-stemmed, freely-flowering, reliable performing, compact, heat-tolerant *Delphinium* plants with dense inflorescences and unique and attractive flower colors.

The new *Delphinium* plant originated from a cross-pollination in the spring of 2019 of the proprietary hybrid selection identified by the hybrid code number SPu1405 (not patented) as the female or seed parent and the proprietary hybrid selection identified as hybrid code number SPu1106 (not patented) as the male or pollen parent. The new *Delphinium* plant was discovered and selected by the Inventor as a single flowering plant from within the progeny of the stated cross-pollination in a controlled greenhouse environment in Whanganui, New Zealand and assigned the hybridizer code SPu1803 during the evaluation process before selecting the cultivar name 'Violets Are Blue'.

Asexual reproduction of the new *Delphinium* plant initially by division in Whanganui, New Zealand starting in 2019 and since 2021 by in vitro meristem culture in a laboratory in Vietnam has shown that the unique features of this new plant are stable and reproduced true to type in successive generations.

BRIEF SUMMARY OF THE INVENTION

The following traits have been repeatedly observed and are determined to be the unique characteristics of *Delphinium* 'Violets Are Blue'. These characteristics in combination distinguish 'Violets Are Blue' as a new and distinct *Delphinium* plant:

1. Compact and sturdy plant habit;
2. Large flowers with semi-double purple petals and ruffled bluish edge;
3. Flower center has purple and white bee;
4. Freely flowering habit not requiring vernalization;
5. Strong upright flowering stems with heavy branching not requiring staking;
6. Excellent garden performance.

The female parent is slightly shorter in habit, the petals are narrower, less ruffled for a shorter period, lack the blue petal margin, and the bee is more distinctly yellowish. The male parent has petals with less blue and less ruffling around the margin.

The nearest comparison cultivars are 'ET DLP 807' U.S. Plant Pat. No. 34,675, the seed cultivar 'Mini Stars' (not patented), and the seed cultivar 'Guardian Blue' (not patented). 'ET DLP 807' is slightly shorter in habit, the petals are flatter and less ruffled, and the bee is more purplish. 'Mini Stars' has shorter plants, with smaller flowers, without ruffled petals, and fewer flowers per stem. Plants of 'Guardian Blue' have a taller habit and flowers that are less ruffled.

BRIEF DESCRIPTION OF THE DRAWINGS

The accompanying color drawings illustrate the overall appearance of the *Delphinium* plant showing the colors as true as it is reasonably possible to obtain in colored reproductions of this type. Colors in the drawings may differ slightly from the color values cited in the detailed botanical description which accurately describe the actual colors of the new *Delphinium* plant. The drawings are of one-year-old plants grown in Zeeland, Michigan.

The drawing on the first sheet (FIG. 1) is a landscape view of three plants in flower.

Figure 1:
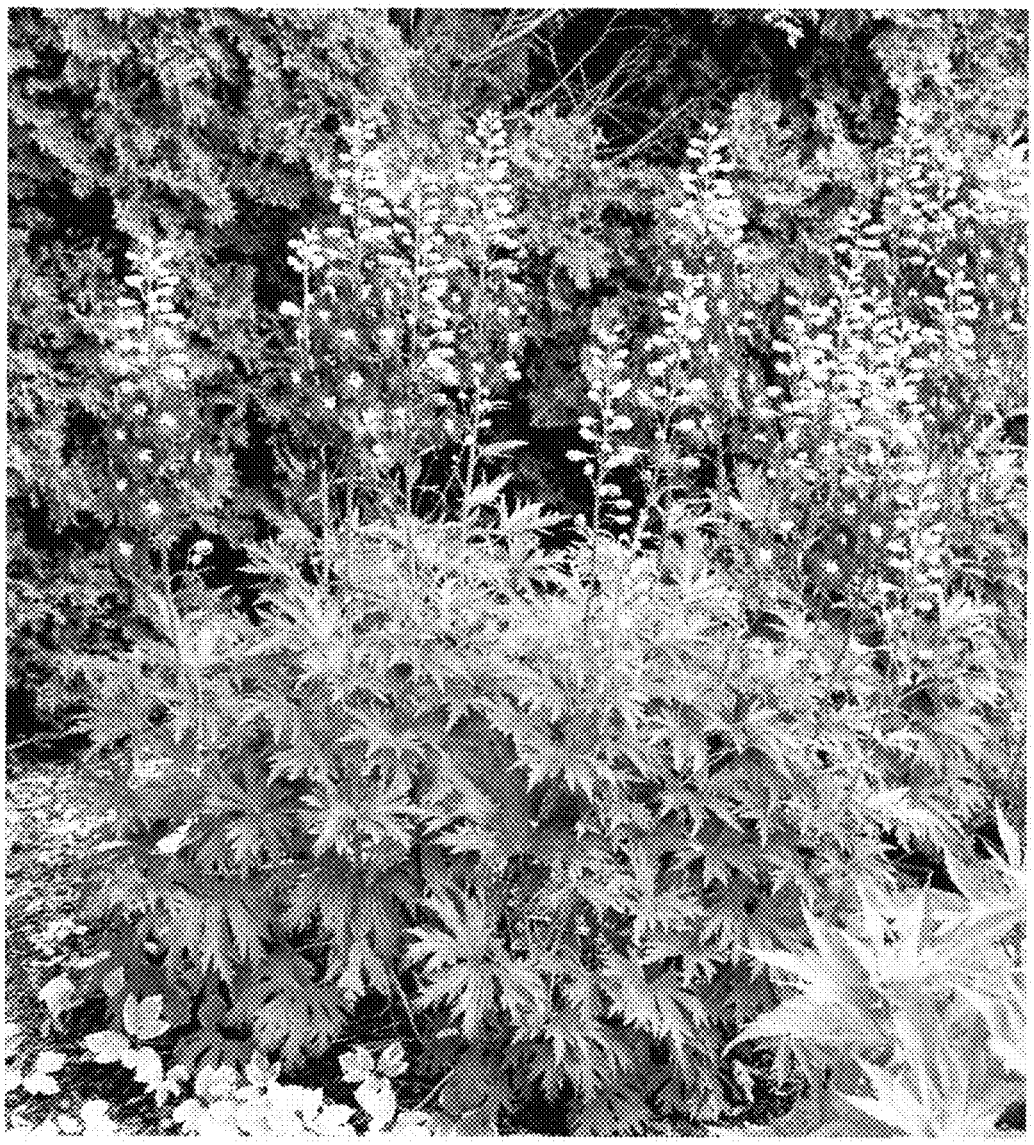
Figure 2:
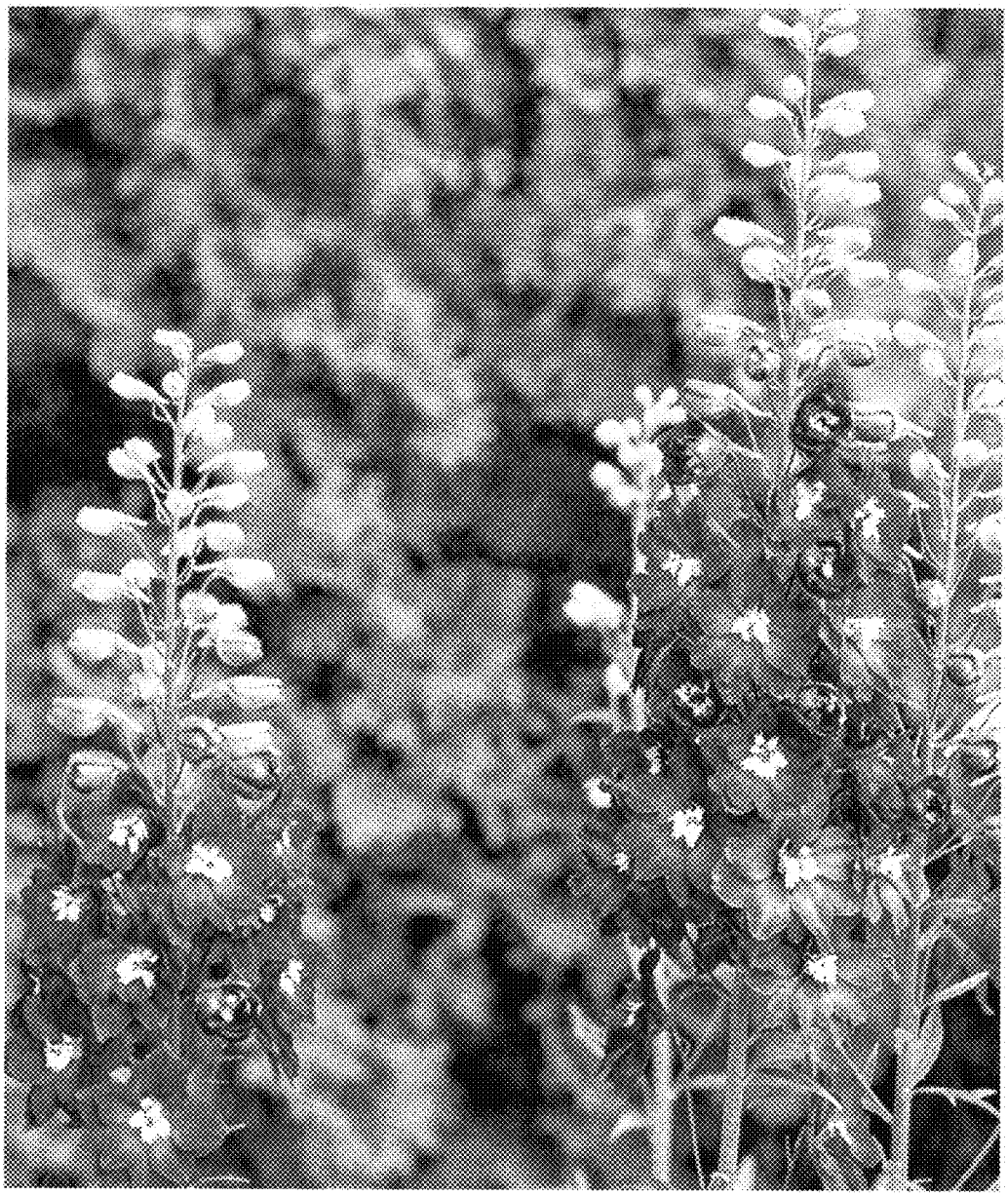

The drawing on the second sheet (FIG. 2) is a close-up view of a typical inflorescence of 'Violets Are Blue'.

DETAILED BOTANICAL DESCRIPTION

The one-year-old plants used for the following description were grown in a partially shaded greenhouse in Zeeland, Michigan with supplemental fertilizer and no plant growth regulators. In the following description, color references are made to The Royal Horticultural Society Colour Chart, 2015 Edition, except where general terms of ordinary dictionary significance are used.

Botanical classification: *Delphinium elatum;*

Parentage: The female parent is the proprietary hybrid selection identified as SPu1405; the male or pollen parent is the proprietary hybrid selection identified as SPu1106;

Propagation: In vitro shoot tip culture;

Time to initiate roots: Summer about 12 to 16 days at temperatures ranging from 15° C. to 21° C., winter about 15 to 25 days at temperatures ranging from 5° C. to 10° C.;

Time to produce a rooted young plant: Summer about four weeks at temperatures ranging from 18° C. to 21° C.; winter about five to six weeks at temperatures ranging from 12° C. to 15° C.;

Root description: Medium in thickness; fibrous; freely branching; typically creamy-yellow in color, actual color of the roots is dependent on substrate composition, water quality, fertilizer type and formulation, substrate temperature and physiological age of roots;

Rooting habit: Freely branching; medium density;

Plant description: Herbaceous winter-hardy perennial; with compact mounded foliage and highly-branched sturdy panicle;

Plant growth rate: Vigorous; finishing from a vernalized plant to flower in about ten weeks in a 3.8-liter container;

Plant height: About 28 cm to top of foliar plane; about 88 cm to the top of floral plane;

Plant width: About 44 cm;

Stem: Cylindrical; glaucous; puberulent in the proximal one-third and glabrous in the distal two-thirds; about 14 cm long before floral branches;

Stem strength: Strong; not requiring staking for wind protection;

Stem color: Closer to RHS 138B than RHS 138A; nodes closer to RHS 138B than RHS 138A;

Internode length: About 8 mm to 9 mm;

Leaf description: Single; alternate; palmately lobed with four to seven main lobes dissected about two-thirds to three-quarters of the way to the petiole; main lobes dissected into three smaller lobes; overall leaf shape roughly reniform; apex acute; base cordate; margins micro-ciliolate and strongly serrate with teeth to about 7 mm long and 5 mm wide at base; adaxial surface lustrous and glabrous; abaxial surface matte and sparsely puberulent; Leaf size: to about 27 cm wide and 18 cm long;

Venation: Palmate; adaxial slightly sunken and glabrous; abaxial costate and puberulent;

Vein color: Adaxial near petiole nearest RHS 145A, near apices between RHS NN137A and RH S139A, and center of the leaf nearest RHS 146C;

Petioles: Slightly applanate top to bottom; glaucous; pubescent in the proximal one-third of the stem and glabrous in the distal two-thirds; base clasping; strong and stiff; to about 13.5 cm long, 1.8 cm wide at stem, and about 0.7 cm wide just before stem;

Petiole color: Adaxial nearest RHS 138B, abaxial nearest RHS 138A;

Inflorescence: Panicle, highly branched in the proximal portion; main stem flowering 60 cm long and 8 cm wide; compound branches in the lower 7 cm diameter below lowest flowers about 9 mm; total inflorescence to about 30 cm wide;

Flower description:

Flower arrangement and shape: Double star-shaped flowers arranged on dense terminal panicle;

Flower aspect: Outwardly;

Flowering habit: Freely flowering; with about 60 flowers per main stem; primary branches to about 55 cm long and 5 mm diameter at base with about 30 flowers per primary branch; up to four secondary branches to about 15 cm long with about 16 flowers per secondary branch; about 250 flowers per main stem including branches;

Flower fragrance: None detected;

Flowering season: Long flowering period; plants flower during the spring through summer in New Zealand with a pause of two to six weeks between the two or three flushes per year; Flower longevity: flowers last about ten to fourteen days on the plant or as a cut flower; flowers not persistent;

Flower buds: Ovoid; rounded apex with rounded base and protruding acute basal spur; puberulent; main bulb to about 20 mm long, 15 mm across, with spur about 15 mm long and 5 mm across at base;

Bud color: Exposed sepal edges nearest RHS 93C; sepal apices between RHS 95C and RHS N95D; sepal midrib nearest RHS 137C;

Flower: Double, with two whorls of sepals typically five sepals per whorl, rarely six, and a dorsal spur, Flower size: To about 7.5 cm diameter and about 4.5 cm deep including spur extending about 2.3 cm; decreasing distally;

Perianth: Typically in three whorls; the outer whorl comprising five to rarely six sepals imbricate in the proximal 5 mm, the center whorl with seven to nine petals imbricate in the proximal two-thirds of the petal, and an inner most whorl comprising about four guard petaloids and four nectiferous petaloids;

Sepals: Ovate to obovate, acute apex, truncate base, entire margin, adaxial glabrous and matte, abaxial glabrous along margin, puberulent in central portion, mostly flat;

Sepal size: To about 22 mm wide and 40 mm long, decreasing in distal flowers; inner whorl to about 17 mm wide and 33 mm long;

Sepal color: When initially open adaxial distal margin portion between RHS N88A and RHS N89C, central portion nearest RHS N87A and inner portion nearest RHS N87C with base between RHS 138A and RHS 146D, abaxial distal margin between RHS N89B and RHS 95B, middle portion nearest RHS 90A, and center midrib nearest RHS 146B distally and blending between RHS 146C and RHS 90B in the middle and proximal portion; when mature and before abscising adaxial proximal two-thirds nearest RHS 86D, distal one-third between RHS 94A and RHS 95B, apical 3 mm nearest RHS 98A, and basal 1 to 2 mm nearest RHS 144B; when mature and before abscising outer whorl abaxial longitudinal center between RHS 91B and RHS 91C, margins between RHS 93B and RHS 93C, basal 1 to 2 mm nearest RHS 144B, with a 3 mm diameter spot 2 mm from the apex nearest RHS 143A;

Sepal spur: Abaxial puberulent, fistulous with acute apex;

Sepal spur size: To about 25 mm long and 5 mm diameter at base of sepal;

Sepal spur color: When initially open nearest RHS 157A, when mature and before abscising nearest RHS 90C proximally and distally nearest 85C;

Petals: Inner whorl ovate to obovate, acute apex, truncate base, entire margin, adaxial and abaxial glabrous and matte, undulate to sinuate in the distal one-quarter; roughly obovate; imbricate; apex acute; base attenuate;

Petals size: To about 17 mm wide and 33 mm long, decreasing in distal flowers;

Petal color: When initially open adaxial distal margin portion between RHS N88A and RHS N89C, central portion nearest RHS N87A and inner portion nearest RHS N87C with base between RHS 138A and RHS 146D, abaxial distal margin between RHS N89C and RHS N89B, middle portion between RHS 90C and RHS N88C, and base nearest RHS 146C; when mature and before abscising adaxial proximal three-quarters nearest RHS N87C, distal one-quarter between RHS 99B and RHS 94A, basal 1 to 2 mm nearest RHS 144B, abaxial proximal three-quarters nearest N87D, distal one-quarter between RHS N88B and RHS N89C;

Petaloids: Typically four guard petaloids in lower portion and four nectiferous petaloids surrounding the stamens and pistils; guard petaloids obovate; adaxial portion about 2 mm to 5 mm from apex puberulent with hairs between RHS 8B and RHS 8C, to about 27 mm long and 12 mm across decreasing in size on distal flowers, with apex emarginate to about 4 mm deep, base attenuate; nectiferous petaloids to about 15 mm long and 3 mm long, decreasing in size distally; apex emarginate to about 2 mm deep; base 9 mm tubular, with middle 10 mm deeply furrowed:

Petaloid color: When opening, adaxial and abaxial apical 2 to 3 mm between RHS N88B and RHS N89A, basal 5 mm nearest RHS 144B, center portion variable nearest RHS 91D and RHS NN155D; when mature and prior to senescing distal portion becoming between RHS N88A and RHS N89A, proximal portion nearest RHS 144C and center portion nearest RHS NN155D;

Peduncles: Cylindrical; to about 72 cm long and about 1.5 cm diameter; erect, stiff, strong; smooth, glabrous, matte;

Peduncle color: Closer to RHS 138B than RHS 138A;

Pedicels: Cylindrical; glaucous; glabrous; to about 16 cm long and 5 mm across at base, decreasing distally to about 5 cm long and 1 mm diameter at base; aspect upright, about 30 degrees angle below vertical in proximal pedicels and about 45 degrees below vertical in distal pedicels; strength strong;

Pedicel color: Nearest RHS 137A;

Reproductive organs:

Gynoecium: Typically four pistils per flower;

*Pistil*.—About 7 mm long.

*Style*.—Acute; tapering to stigma; about 3 mm long and 0.5 mm wide at base.

*Style color*.—Nearest RHS 157D.

*Stigma*.—Globose; about 0.2 mm long and 0.2 mm diameter.

*Stigma color*.—Nearest RHS NN155B.

*Ovary*.—Conical; lustrous; about 3.5 mm long and 2 mm across near base.

*Ovary color*.—Between RHS N144A and RHS 144C.

Androecium: About 28 to 36 per flower;

*Filament*.—Applanate, hyaline, to about 1.5 mm wide and 5 mm long in the proximal half; filiform, to about 4 mm long and 0.2 mm in distal half.

*Filament color*.—Nearest RHS NN155B.

*Anther*.—Basifixed; longitudinal; oblong; to about 2 mm long and 1 mm across.

*Anther color*.—Between RHS 191A and RHS 160B.

*Pollen*.—Abundant.

*Pollen color*.—Nearest 155A.

Fruit: Typically, three to five aggregate follicles; glabrous; apex beak, about 3 mm long; base sessile; size to about 3 cm long and 1.8 cm across near middle; color as maturing nearest RHS 137B, when dried between RHS 164D and RHS 165D;

Seeds: Typically, 6 to 12 per follicle; irregularly pyramidal to nearly cubical; size to about 2.8 mm across; color variable, between RHS 200A, RHS 202 A, and RHS 199C;

Winter hardiness: To USDA zones 3 to 8;

Garden performance: Flowering raceme is strong and stiff and tolerant of wind and rain; best grown with good drainage soils;

Pest and diseases: Susceptibility or resistance to diseases beyond that typically found in other *Delphinium* plants has not been observed;

I claim:

1. A new and distinct *Delphinium* plant named 'Violets Are Blue' as herein illustrated and described.

* * * * *